United States Patent [19]
Krueger et al.

[11] Patent Number: 5,772,625
[45] Date of Patent: Jun. 30, 1998

[54] EXTERNAL DRAINAGE SHUNT

[75] Inventors: John A. Krueger, Brookfield, Wis.; Kevin M. Jaeger, Lake Bluff; Helmut W. C. Rosenberg, McHenry, both of Ill.

[73] Assignee: Heyer-Schulte NeuroCare, Inc., Pleasant Prairie, Wis.

[21] Appl. No.: 752,731

[22] Filed: Nov. 19, 1996

[51] Int. Cl.$^6$ ...................................................... A61M 5/00
[52] U.S. Cl. .............................. 604/9; 604/317; 128/760
[58] Field of Search ..................................... 604/317, 318, 604/322, 323, 326, 327, 8, 9, 10; 128/767, 768, 760, 748

[56] References Cited

U.S. PATENT DOCUMENTS

| | | | |
|---|---|---|---|
| Re. 26,964 | 10/1970 | Coanda | 128/2 |
| 3,157,201 | 11/1964 | Littmann | 137/625.47 |
| 3,604,420 | 9/1971 | Vaillancourt | 128/275 |
| 3,838,691 | 10/1974 | Paludan et al. | 128/275 |
| 3,906,935 | 9/1975 | Raia et al. | 128/2 F |
| 3,957,050 | 5/1976 | Hines, Jr. | 128/275 |
| 4,029,097 | 6/1977 | LeRoy | 604/326 X |
| 4,103,689 | 8/1978 | Leighton | 128/350 V |
| 4,157,718 | 6/1979 | Baehr | 604/317 X |
| 4,175,558 | 11/1979 | Hess, III et al. | 128/214 C |
| 4,343,316 | 8/1982 | Jespersen | 128/767 X |
| 4,402,682 | 9/1983 | Garver, Sr. et al. | 604/111 |
| 4,435,174 | 3/1984 | Remond et al. | 604/174 |
| 4,500,311 | 2/1985 | Redmond et al. | 604/323 X |
| 4,521,213 | 6/1985 | Steigerwald | 604/323 |
| 4,731,056 | 3/1988 | Tremulis | 604/118 |
| 5,011,469 | 4/1991 | Buckberg | 604/8 X |
| 5,207,661 | 5/1993 | Repschlager | 604/317 |

OTHER PUBLICATIONS

Heyer–Schulte Bulletin No. 102213–001–03–1186; American V. Mueller American Hospital Supply Corporation, Chicago, Illinois 60648.

Neuroscience Products Catalog, ICP Monitoring and CSF Drainage Systems and Accessories, 1989–1990, Cordis Corporation, Miami, FL.

CNS Bulletin, MoniTorr ICP, External Drainage and Monitoring Systems, Clinical Neuro Systems, Clinical Neuro Systems, Inc., Exton, MA 19341.

Codman Bulletin —External Drainage Collection Kit/External Drainage Collection Bag and Tubing Set, Codman & Shurtleff, Inc.

PS Medical —External Drainage Products Catalog No. 46422, Distributed by Cappai Medical, Inc. Atlanta, GA 30328.

*Primary Examiner*—Sam Rimell
*Assistant Examiner*—Luke Yeh
*Attorney, Agent, or Firm*—James A. Geppert

[57] ABSTRACT

A drainage system for use in the drainage of ventricles of a patient's brain or of the patient's lumbar region and which is connected to a catheter inserted in either the ventricles or lumbar region and secured to the patient, the system including tubing from the catheter, a four-way stopcock inserted into the tubing followed by a Y-connector providing a needle-less sampling site, and a one-way valve, a length of flexible tubing leading from the one-way valve to a burette clamped within a sliding panel mounted on a support panel, suspension means for the support panel onto an IV pole, said sliding panel being in frictional contact with the support panel so as to remain in adjusted position on the support panel, and a drainage bag connected to the bottom of said burette to receive the collected fluid from the burette after it is measured. A four-way high flow stopcock is positioned between the burette and drainage bag, and the support panel is provided with two pairs of keyhole slots vertically spaced thereon for ease of replacement of a full drainage bag with an empty drainage bag. Also, a combination bubble level and measuring tape is provided with bent end on the extendable tape for connection to one of a pair of slits in the support panel for ease of system leveling by personnel in surgery.

18 Claims, 10 Drawing Sheets

EXTERNAL DRAINAGE SHUNT

TECHNICAL FIELD

The invention disclosed herein relates to an external drainage unit or system which is adapted for use on a surgical patient to provide a sterile fluid path that is resistant to microbial particles and is utilized to drain cerebrospinal fluid from the ventricles of the brain or the lumbar subarachnoid space to a collection bag.

BACKGROUND

The present invention relates to an external ventricular drainage system for use in the draining of cerebrospinal fluid from the ventricles of a patient's brain to prevent the undue buildup of such fluid and pressure within the brain or utilized in the appropriate drainage of other body cavities. Such external ventricular drainage assemblies are designed for use in the treatment of hydrocephalus wherein excess cerebrospinal fluid is drained from the ventricles of the brain. In many previously known techniques for the treatment of hydrocephalus, excess fluid is drained from the ventricles of the brain to another region of the body, such as the right atrium or the peritoneum. In such systems, a valve mechanism is employed which is implanted in the patient. The valve mechanism permits the flow of the excess fluid from the brain to such other parts of the body.

Under certain circumstances, it is desirable to treat hydrocephalus by draining the excess fluid from the ventricles of the brain to a collection receptacle that is outside the body, such as in the case of surgically induced hydrocephalus which may be only a temporary problem and would not require a totally implanted shunting system. In such a case, an external shunt or drainage system is desirable.

However, problems associated with external drainage systems which drain fluid from the body, regardless of the fluid, generally relate to such systems providing routes of infection to the patient. An external drainage system which is open to the environment surrounding a patient can provide a route for microbes, such as bacteria, to enter the patient's body. As it is undesirable to have the possibility for the introduction of bacteria to cause an infection to a patient who may already be in a weakened condition. Thus, it would be desirable to provide an external ventricle drainage assembly which would prevent or inhibit the introduction of bacteria and other microbes into the patient and which would be an easy-to-use system.

A study was made of surgical procedures for patients wherein drainage systems were utilized or necessary, and surgeons and surgical nurses were consulted for their input as to objections and problems in presently known and used external drainage systems and the information acquired from these interviews and studies were incorporated into the external drainage system set forth in the present application and to which the present invention is directed.

SUMMARY OF THE INVENTION

The present invention relates to a novel and unique external ventricle drainage system that is easy to use and provides benefits not found in presently known commercially available systems. In one instance, the drainage assembly attaches to a ventricle drainage catheter which is inserted into the ventricles of the patient's brain and is anchored to the patient after it extends to the exterior of the patient to prevent relative movement between the patient and the catheter. The assembly includes tubing connected to the catheter which is provided with a one-way valve positioned within the patient line or tubing following a needleless port for aspiration, injection or priming the system. A support panel is provided downstream of the first needleless port which is mounted on a support pole and carries a burette chamber, a second needle-less port downstream of the burette chamber, and a drainage bag is connected to the lower end of the burette chamber through the second port.

Other novel aspects of the present invention are concerned with a burette chamber that is marked for increments of from zero to fifty milliliters with one to twenty fine differentiable increments of less than one milliliter. Also, the drainage bag has a capacity of seven hundred milliliters with an anti-microbial filter and slide clamp, a large bore flow path from the burette to facilitate rapid fluid drainage, and a dual-bag hanging post on the support panel allowing one person to exchange drainage bags; the bag and panel having a positive locking position bag hanging design. Further, the width of the support and sliding panels are designed to be easily manipulated with one hand. Also, there is a three-way stopcock below the burette to provide exact, repeatable burette volumetrics.

All loose components are tethered to eliminate the potential of dropping caps. The cord suspension is accomplished in a planar field (three points) to minimize rotational movements when the system is suspended as compared to two-point linear suspension systems. The patient line has a white-stripe thereon to differentiate the neuro-drainage line from other patient lines as well as providing a reference background to view CSF clarity. The system provides three places for strain relief of excess tubing, and the system is able to mount to IV poles without the addition of a clamping device.

BEST MODES OF CARRYING OUT THE INVENTION

Figures 1, 4, 5, 6:
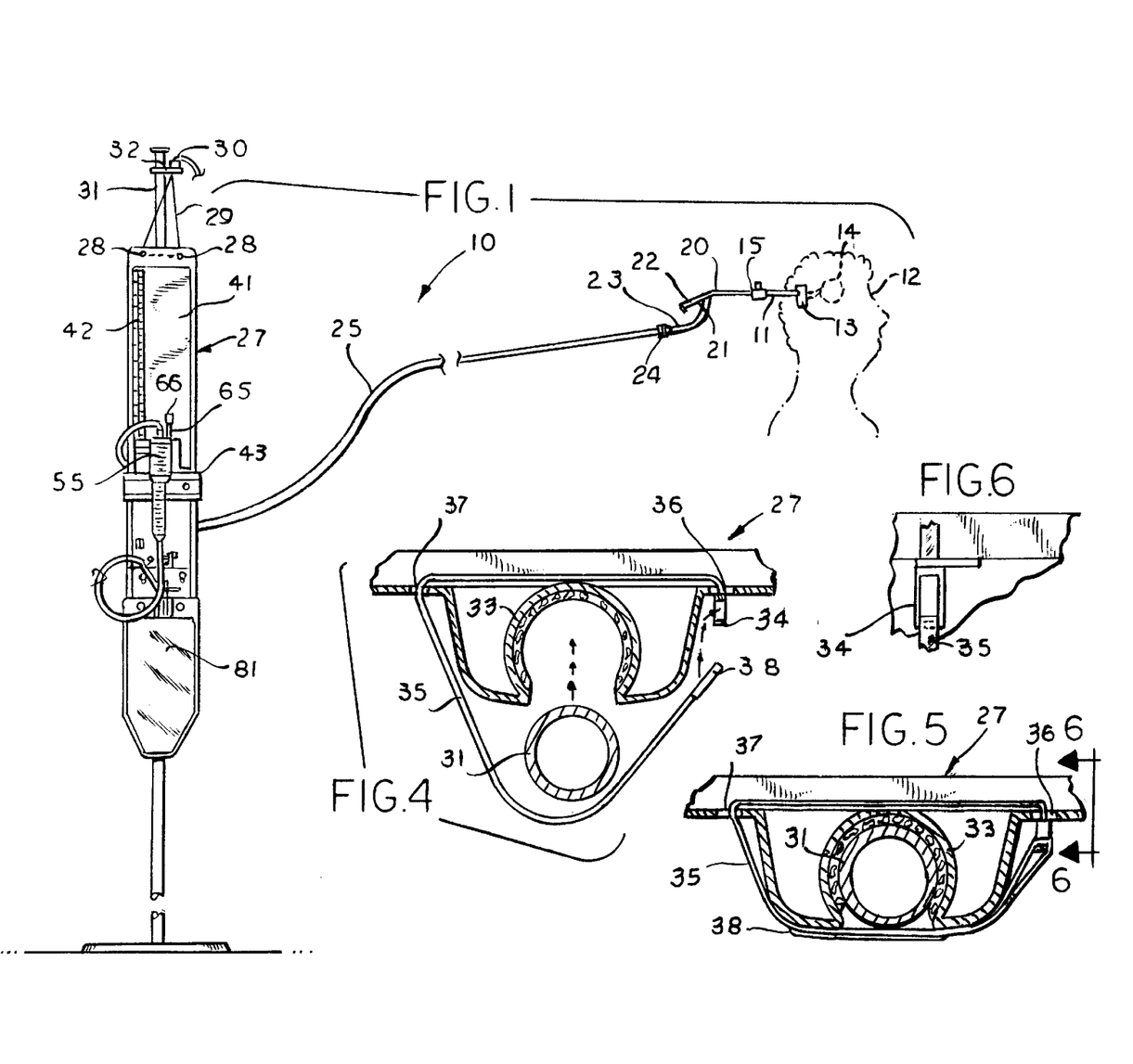
FIG. 1 is an elevational view of the external ventricle drainage assembly attached to a patient.
FIG. 4 is a horizontal cross sectional view of the attachment means for the support panel to an IV pole taken on line 4—4 of FIG. 3.
FIG. 5 is a cross sectional view similar to FIG. 4 but showing the panel attached to the IV pole.
FIG. 6 is a partial cross sectional view taken on line 6—6 of FIG. 5.

Referring more particularly to the disclosure in the drawings wherein is shown an illustrative embodiment of the present invention, FIG. 1 discloses an external drainage assembly 10 for a surgical patient including tubing 11 which is attached to a suitable catheter in the form of a ventricle drain, the catheter being attached to the head 12 of the patient by a suture tab 13 to prevent relative movement between the catheter and patient. The catheter extends from the ventricles 14 outwardly of the patient's skull through a suitable burr hole and along and under the scalp to an exit site; wherein the catheter then extends outwardly of the patient and is attached to the tubing 11 through a suitable connector. It may desirable to provide a catheter guide (not shown) for holding the catheter in position within the patient's brain.

Just beyond the exit of the catheter from the patient's scalp is a four-way patient line stopcock 15 (FIGS. 12 through 15) which provides a catheter port 16, an ICP monitoring port 17 and a Y-connector port 19 controlled by a handle 18. This valve is followed by a length of tubing 20 terminating in a Y-connector, needle-less valve assembly 21 having a sampling site 22. Tubing 23 downstream of the valve assembly contains a low-pressure, one-way valve 24 to help prevent reflux of fluid into the ventricles or lumbar subarachnoid space.

Figures 2, 3:
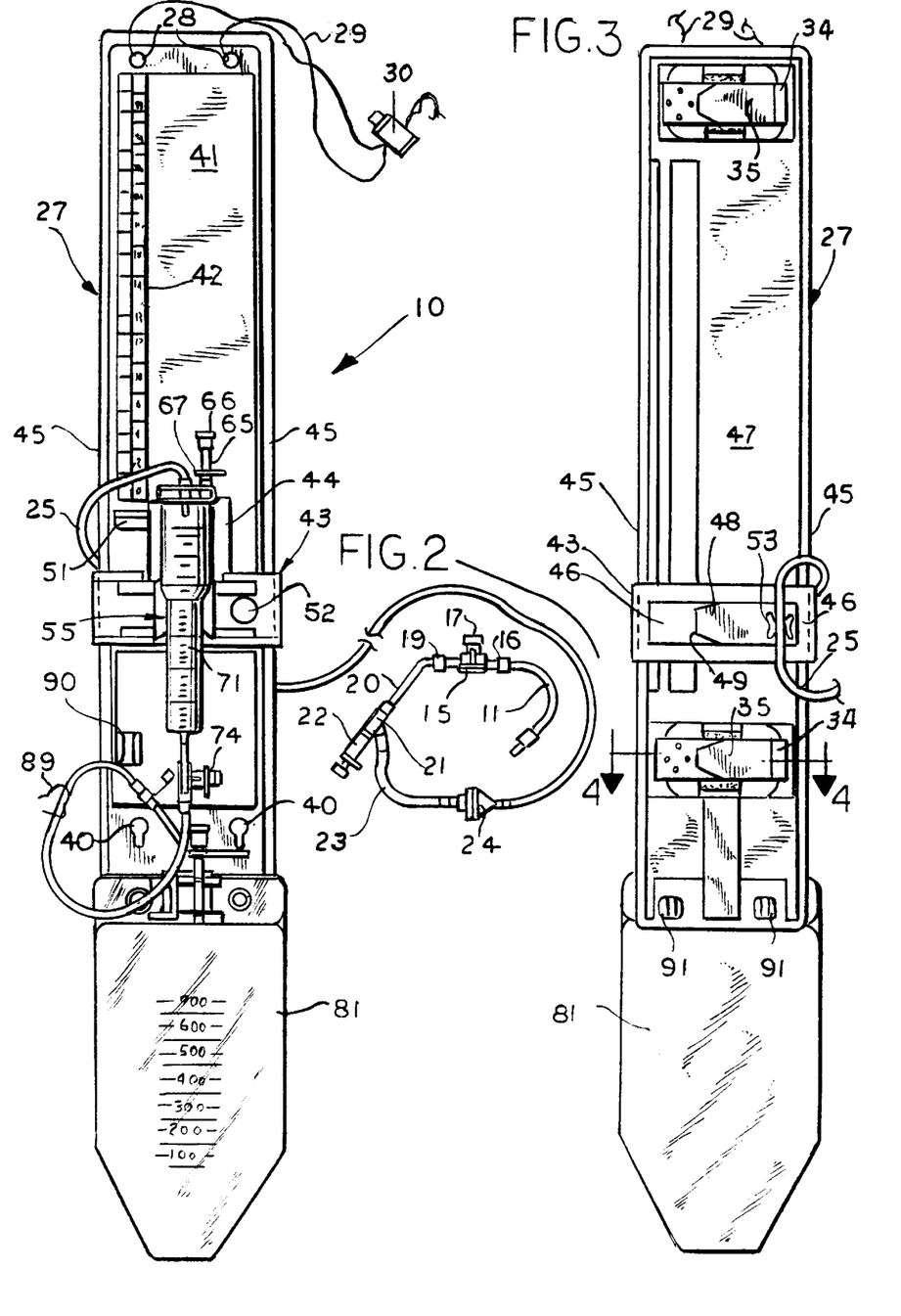
FIG. 2 is a front elevational view of the support panel attached to the drainage line for the patient.
FIG. 3 is a rear elevational view of the support panel.
Figures 7, 8, 9:
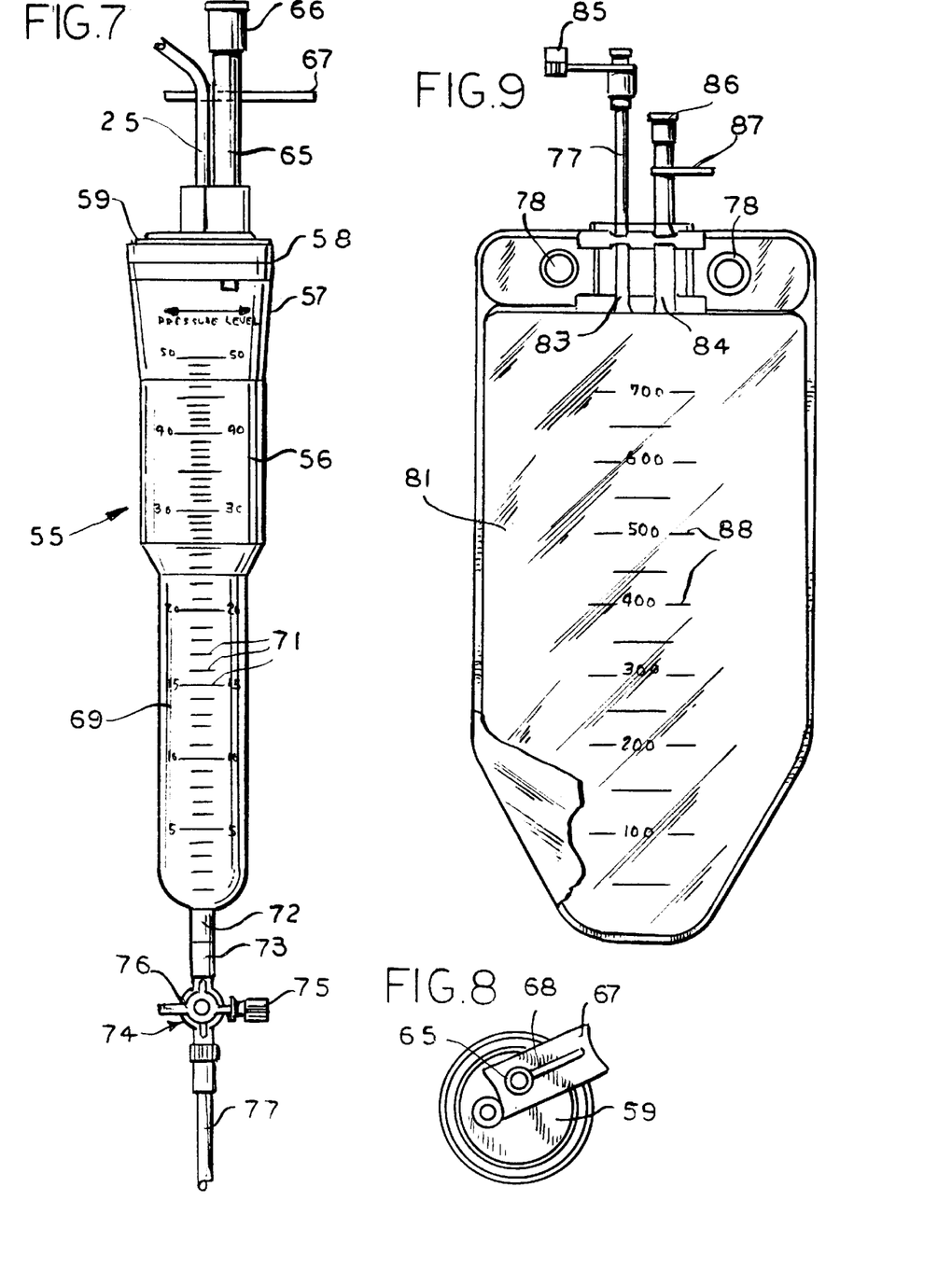
FIG. 7 is a front elevational view of the burette used on the support panel.
FIG. 8 is a top plan view of the burette and tubing clamp for the line leading thereto.
FIG. 9 is a front elevational view of the drainage bag for attachment to the bottom of the support panel.

Beyond the one-way valve 24, a substantial length of tubing 25 leads to a collection burette 55 mounted on a support panel 27 for collection and measurement of the fluid collected from the patient. The support panel is a substantially rigid, elongated and generally rectangular panel having a pair of openings 28 adjacent the upper edge to receive a suspension cord 29 for suspension from the upper arm of 32 of an IV pole 31. Formed on the rear surface of the support panel are a pair of spaced pole clamps 33, 33 adapted to frictionally receive the support pole 31; each clamp being provided with a strap 35 having a loop 34 at one end. The strap extends through a slot 36 in the panel, behind the panel and outwardly through a second slot 37. The strap 35 is laid over the pole 31 and clamp 33, extends through the loop 34 and is reversed to extend over the intermediate strap portion and the pole and clamp and fastened with a "Velcro" fastener 38. Adjacent the lower edge of the panel 27 are two pairs of vertically spaced, keyhole-shaped openings 39,39 and 40,40 providing a support for a drainage bag 81; the two pairs of openings being utilized during the replacement of a filled bag for a new empty bag. Within the borders of the panel and sandwiched between layer thereof is a suitable placard 41 having instructions for use of the drainage apparatus and pressure scales 42 along one vertical edge.

Figures 10, 11, 12:
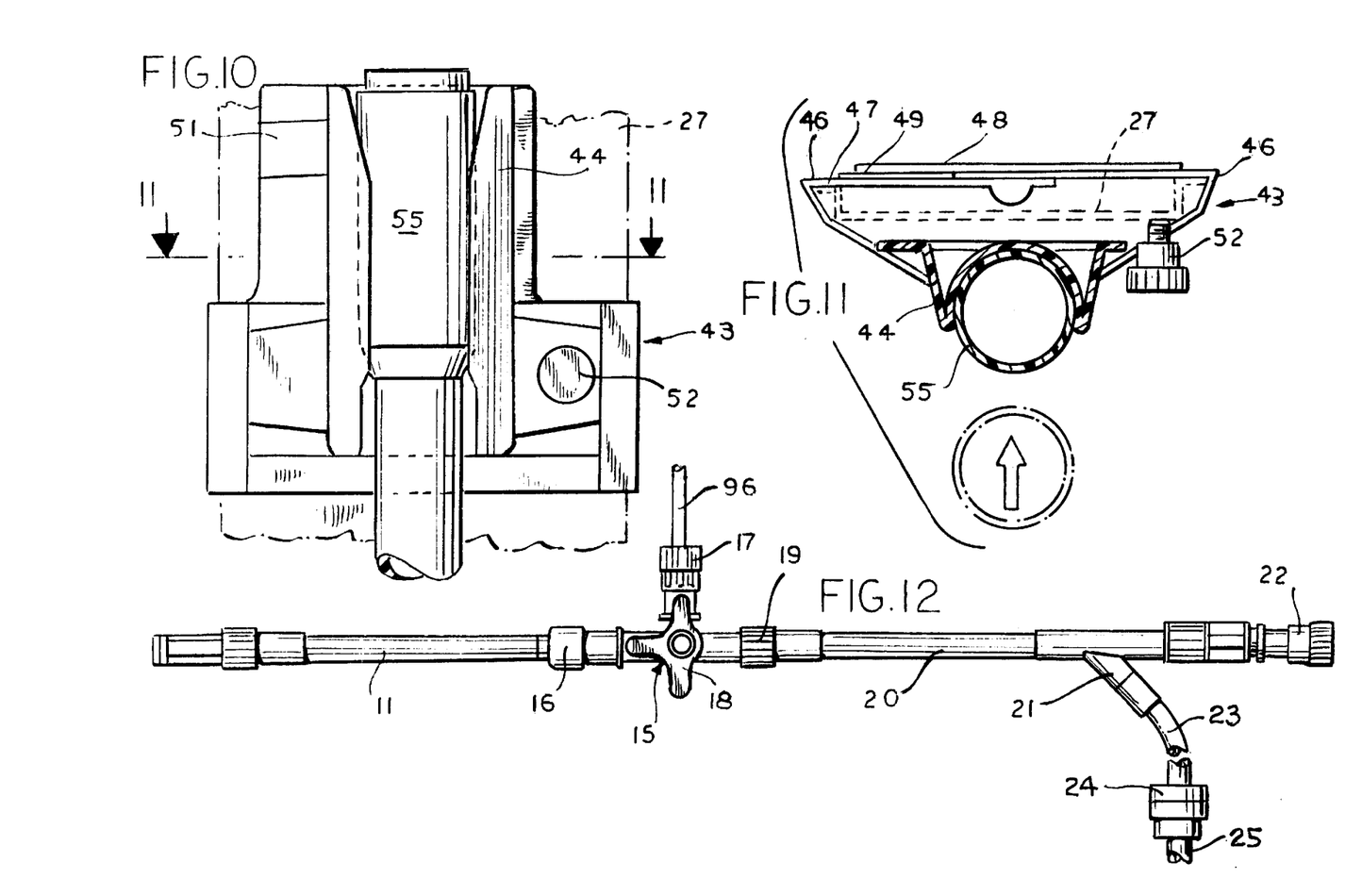
FIG. 10 is an enlarged partial front elevational view of the slidable panel on the support panel showing the clamp receiving the burette.
FIG. 11 is a horizontal cross sectional view taken on line 11—11 of FIG. 10.
FIG. 12 is an enlarged plan view of the four-way valve in a monitoring position positioned in the tubing adjacent the patient's head.
Figure 13:
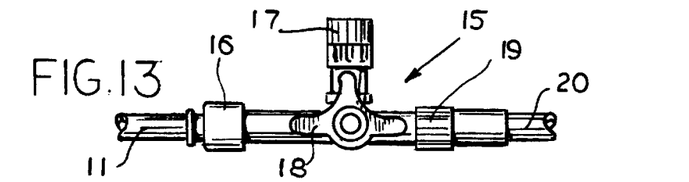
FIG. 13 is an enlarged view of a four-way valve shown in FIG. 12 with the valve in a second position.
Figure 14:
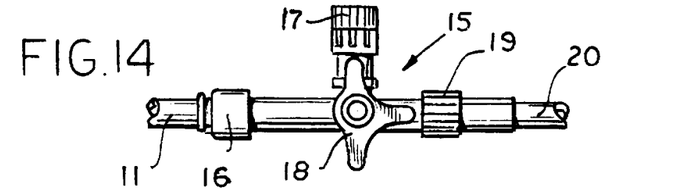
FIG. 14 is a view similar to FIG. 13, but showing the valve in a third position.
Figure 15:
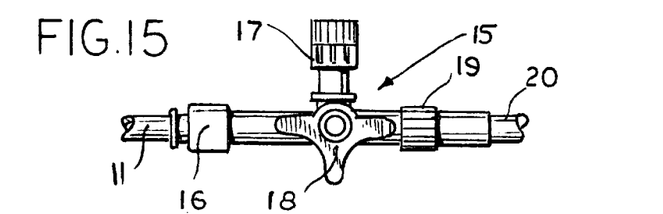
FIG. 15 is a view similar to FIG. 13, but showing the valve in a fourth position.
Figures 16, 17, 18:
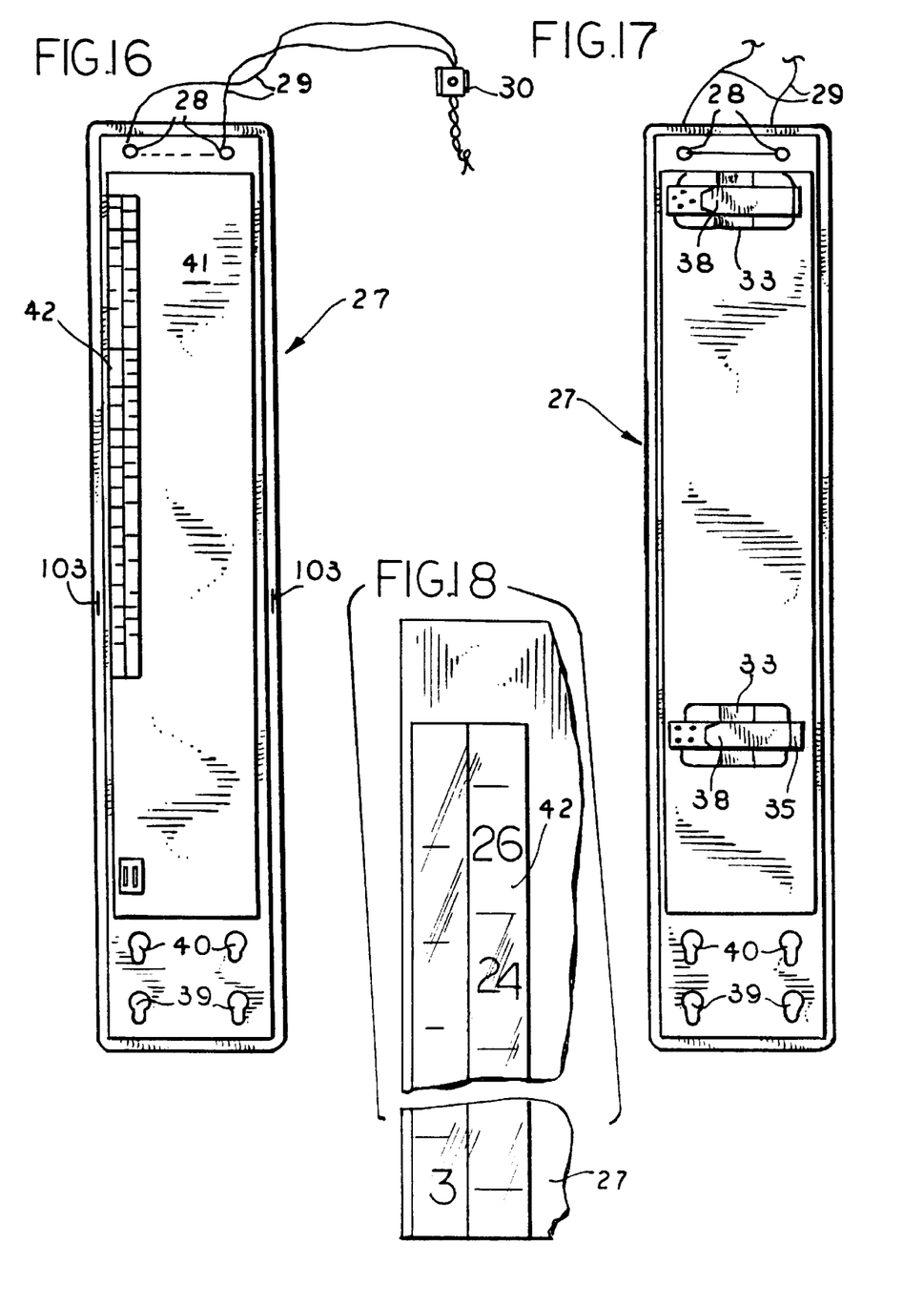
FIG. 16 is a front elevational view of the support panel with the slidable panel, burette and drainage bag removed.
FIG. 17 is a rear elevational view of the support panel seen in FIG. 16.
FIG. 18 is an enlarged partial front elevational view of the support panel showing the scale for pressure readings.
Figure 19:
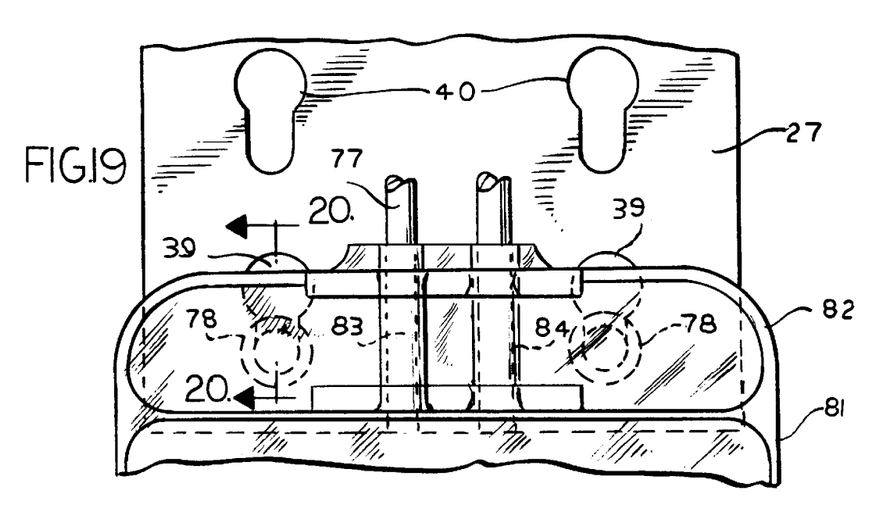
FIG. 19 is a front elevational view of the lower end of the support panel and upper portion of the drainage bag showing the mounting for the bag.
Figures 20, 21, 22:
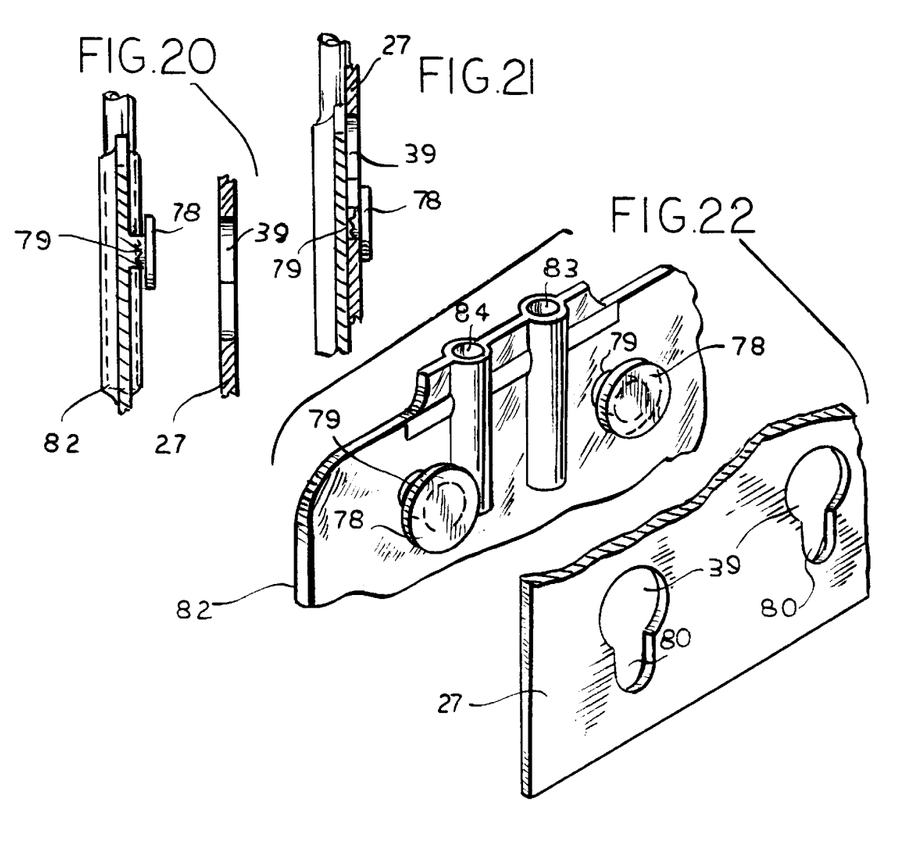
FIG. 20 is a partial vertical cross sectional view taken on line 20—20 of FIG. 19 with the bag and support disassembled.
FIG. 21 is partial cross sectional view similar to FIG. 20, but showing the bag and panel assembled.
FIG. 22 is an exploded rear perspective view of a portion of the disassembled bag and panel.
Figure 23:
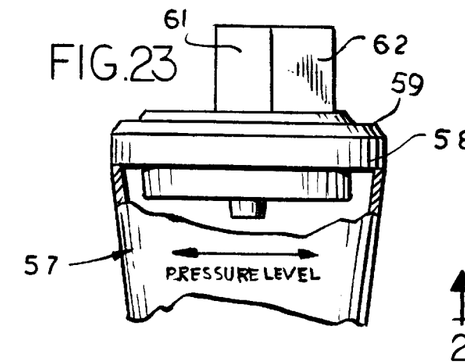
FIG. 23 a front elevational view of the burette upper end.
Figure 24:
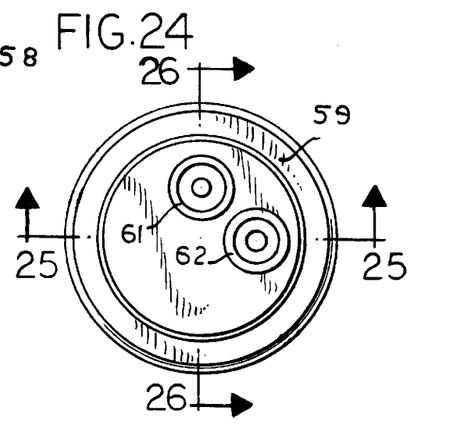
FIG. 24 is a top plan view of the burette upper end.
Figure 25:
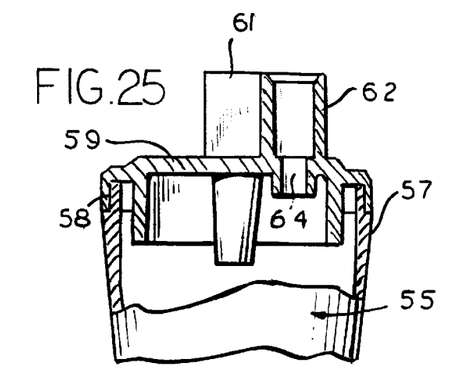
FIG. 25 is a partial vertical cross sectional view taken on line 25—25 of FIG. 24.
Figure 26:
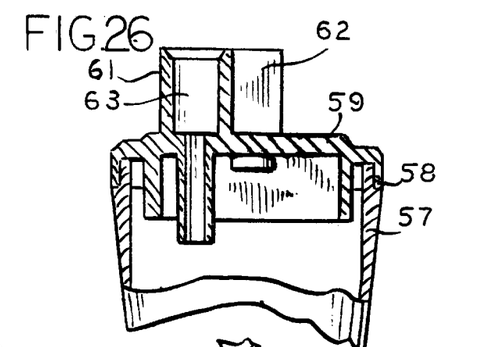
FIG. 26 is a partial vertical cross sectional view taken on line 26—26 of FIG. 24.

A sliding panel 43 which extends across the width of the support panel 27 has a U-shaped clamping portion 44 centrally located to receive a drainage burette 55 for connection to the tubing. The sliding panel extends across the support panel 27 and includes arms 46 which are folded around the support panel edges 45 and extend across the rear surface 47 of the support panel 27 with the ends 48 overlapping and suitably secured together by a snap fit and adhesively bonded at 49; the wrapping of the sliding panel 43 around the support panel 27 providing frictional contact to retain the sliding panel in any desired vertical position on the panel. A sight window 51 is located in the panel 43 generally aligned with the pressure scales 42 on the placard. A locking knob 52 may project through and threadingly engage the sliding panel with a threaded end which extends inward through the panel 43 to contact the surface of the support panel 27 and positively lock the sliding panel in its adjusted position. Also formed on one panel arm 46 is a bonded tubing relief rib 53 (see FIG. 3) to clamp a portion of the tubing 25 and prevent kinking and unwarranted bending of the tubing while the sliding panel is adjusted.

The burette 55 has a generally cylindrical upper body 56 terminating at its upper end with a flared portion 57 having a shouldered open end 58 receiving a cover or cap 59 to seal the upper end; the cover being provided with a pair of cylindrical projections 61 and 62 forming a pair of passages 63 and 64, respectively. One passage 63 is connected with the end of the tubing 25 to collect the fluid draining from the patient; while the second passage 64 is connected to vent tubing 65 for venting the burette and has a vent cap or filter 66 on the end thereof to prevent entry of air-born bacteria or other contaminating matter into the burette. A slide tubing clamp 67 having an elongated generally V-shaped opening 68 is also positioned on the tubing 65 and shiftable relative to the tubing to prevent fluid within the burette from reaching the filter, if engaged.

Figures 27, 28, 29:
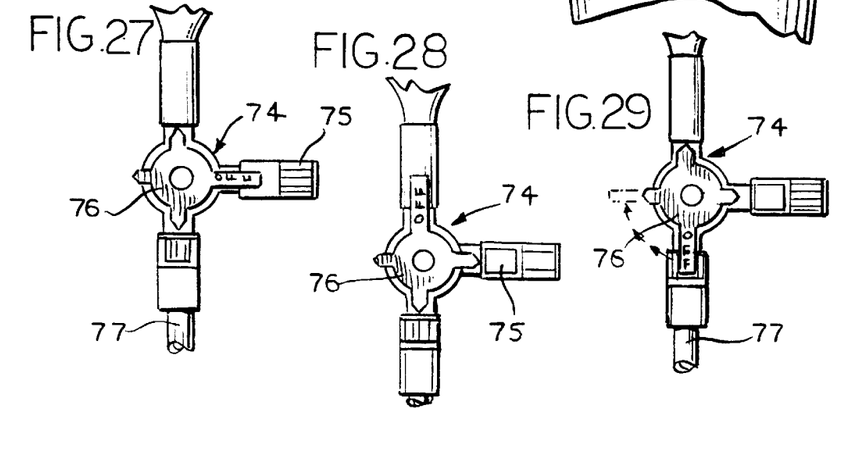
FIG. 27 is an elevational view of a high-flow four-way valve used in the drainage system between the burette and the drainage bag showing the valve in a first position.
FIG. 28 is an elevational view similar to FIG. 27, but showing the valve in a second position.
FIG. 29 is an elevational view similar to FIG. 27, but showing the valve in a third position.
Figure 30:
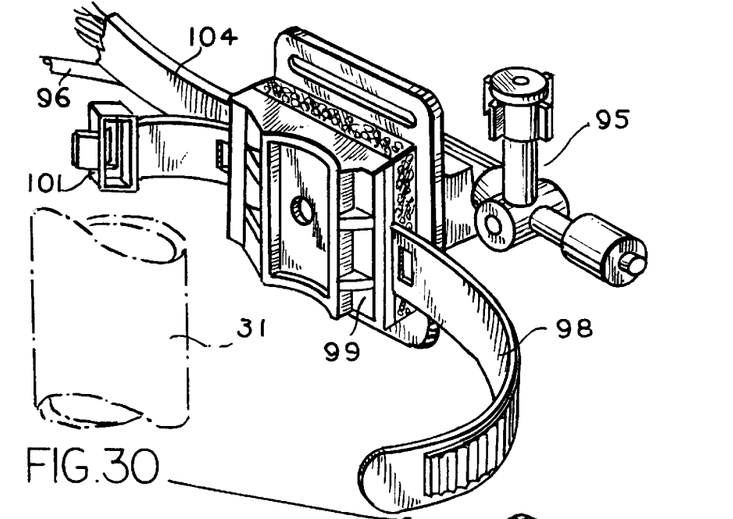
FIG. 30 is an enlarged perspective view of a mounting for a fluid-filled transducer mounted on the support panel.
Figure 31:
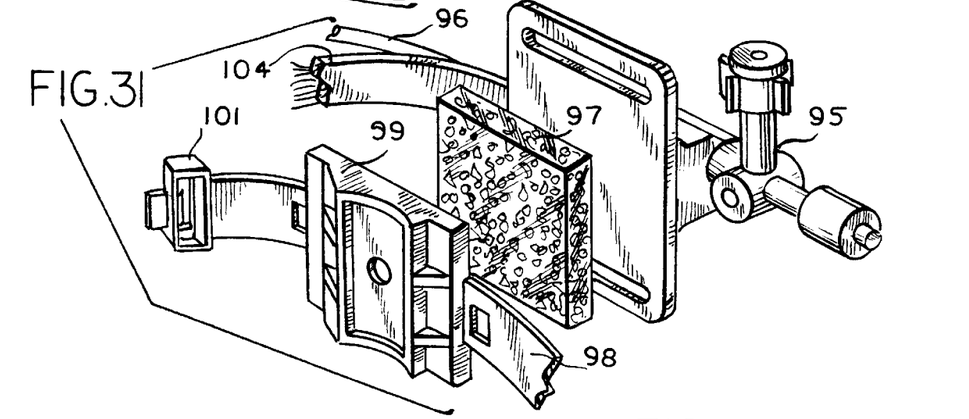
FIG. 31 is an exploded enlarged perspective view of the transducer mounting of FIG. 30.
Figure 32:
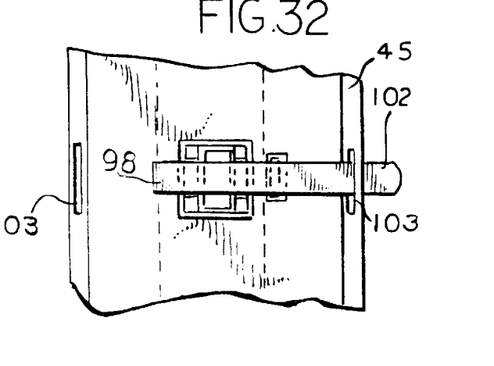
FIG. 32 is a showing of the positioning of the transducer mounting on the support panel.
Figure 33:
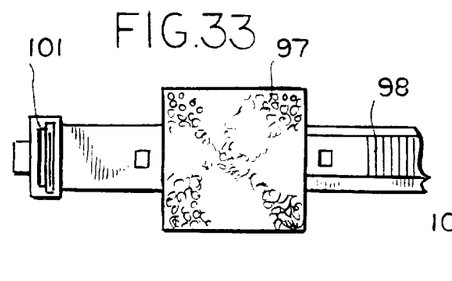
FIG. 33 is a front view of the mounting strap.

The lower approximately one-half 69 of the burette 55 is of a lesser diameter than the upper body 56 so as to provide greater gradations 71 for greater accuracy of measuring the fluid quantities in the burette. At the lower end of the burette is a full radius drain port 72 which is connected to a high-flow, four-way valve 74 by a short piece of tubing 73. This valve is provided with an off position (FIG. 28), a flow position (FIG. 27) and a sampling position (FIG. 29). A sampling port 75 is located so that a syringe may be inserted into the port and a sample withdrawn. Below the valve, a length of tubing 77 extends from the burette to a drain bag 81 which is suspended from the support panel by a pair of enlarged buttons 78 integral to the upper end of the bag by reduced portions 79 so that the buttons can be received in the lower pair of keyhole openings 39, 39 with the necked-down portions 79 being received in the narrowed port ions 80 of the openings. The drain bag 81 is also provided with a pair of passages 83, 84 extending through the upper closed end 82 of the bag. One passage 83 is connected to the tubing 77 having a tethered cap 85 while the other passage 84 is a venting passage having a vent cap 86 and slide tube clamp 87 thereon. The bag also has volume gradations 88 thereon for measuring the amount of accumulated fluid.

The drainage bag arrangement is designed so that one nurse or other technician can easily replace a filled drain bag 81 with an empty bag as follows. The stopcock valve 76 is rotated to the accumulation or off mode (FIG. 28), the tube clamp 89 proximal to the drainage bag is locked and a replacement bag is mounted in the upper set of openings 40, 40. A tethered cap, like cap 85 in FIG. 9, on the new bag is opened and immediately connected to the tubing 77 removed from the filled bag; the tethered protective cap 85 is connected to passage 83 for the filled bag and the bag is removed from the support panel. Then the replacement bag is either left on the upper set of openings 40, 40 or shifted onto the lower set of openings 39, 39, the clamp 89 is opened and the valve 76 opened to allow communication between the burette 55 and the empty bag. The tubing 77 from the burette 55 to the drainage bag 81 can be secured in retention rib 90 formed on the front on the support panel 27 to prevent kinking of the tubing and strain relief. Also, the patient line 11, 20, 23 and 25 from the ventricles 14 is provided with a white strip (not shown) to differentiate the neuro drainage line from other patient lines and allow visual magnification of CSF clarity.

Mounted adjacent to the rear surface 47 of the support panel 27 is a manifold for a fluid filled transducer 95 utilizing strain gage technology and having a length of pressure sensitive tubing 96 which leads from the transducer to the ICP monitoring port 17 on the valve or stop cock 15 to measure the pressure fluctuations in the tubing line draining fluid from the ventricles of the patient. The transducer is adhesively mounted onto a foam pad 97 which is, in turn, adhesively mounted onto the generally square mounting portion 99 of a mounting strap 98 having a buckle 101 on one end and a free end 102 which is positioned to wrap around the support pole 31, pass through the buckle, and extend to and project through a slit 103 formed in the edge 45 of the support panel 27 corresponding to the "0" pressure level of the scales 42.

Figures 38, 39:
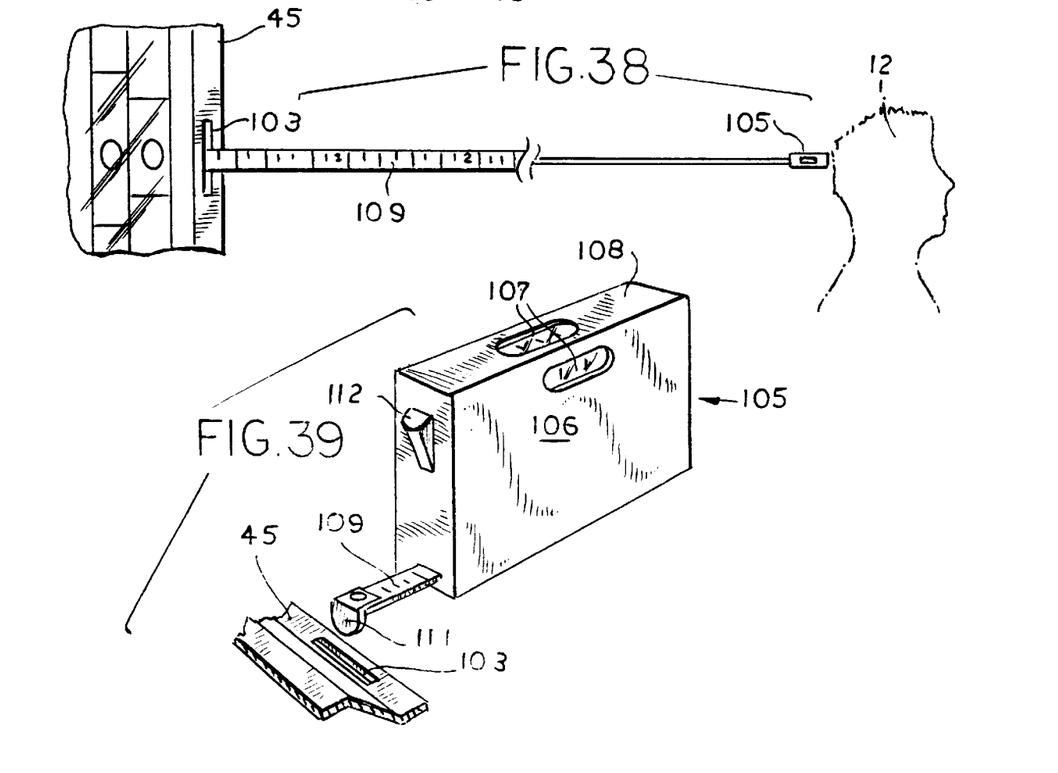
FIG. 38 is a schematic showing of a level/tape measure for use between the patient's head and the support panel.
FIG. 39 is an enlarged perspective view of the level/tape measure of FIG. 38.

Shown in FIGS. 38 and 39 is a level/tape measuring device 105 utilized by a surgical nurse or other technician to determine the positioning of the support panel 27 relative to the patient during surgery. The device 105 includes a housing 106 containing a bubble level 107 positioned at the upper surface 108 of the housing for ease of viewing from the top and sides and a retractable tape measure 109 having a metal tab 111 which is bent over and adapted to be inserted into a slit 103 formed in either edge 45 of the support panel 27; the slit frictionally retaining the tab of the tape measure during measurement to properly place the support panel and sliding panel relative to the patient's head. A locking knob 112 on the housing appropriately locks the tape in its extended position where desired.

In use, the ventricular catheter is introduced into the ventricle 14 or a lumbar catheter is introduced into the lumbar subarachnoid space and the catheter is secured by a suitable exterior suture tab 13. A check is made for free flow of CSF and then the catheter is clamped. The support panel 27 is suspended from the IV pole 31 via the suspension cord 29 and the drainage system height is positioned via the cord lock 30. If the panel is directly connected to the IV pole 31, the pole mount clamps 33 on the back of the support panel 27 are pushed onto the IV pole and secured in place by the "Velcro" connection of straps 35 (FIGS. 5 and 6). The straps should be securely tightened or the support panel may slip. Once the straps are secured, tighten the suspension cord 29 by moving the cord lock 30 so the cord is taut, and ensure that the system has been properly mounted and leveled with the zero point of the reference scale 42 aligned to the patient's Foramen of Monro.

The external portion of the drainage system must be primed before connecting to the catheter by using a syringe with sterile saline solution having the air bubbles eliminated, which is connected to the patient line needle-less valve sampling site 22 at the Y-connector 21. The handle 18 of the stopcock is rotated to the position of FIG. 13 and the saline solution is injected into the system. The valve handle is repositioned to the position of FIG. 14 and additional fluid is injected until flow is observed in the drip chamber or burette and the syringe is removed from the needle-less port. To then drain the CSF, the handle is turned to the position of FIG. 15 or, in the alternative, the position of FIG. 14. To accumulate the CSF in the burette chamber, the handle 76 of the four-way valve 74 is turned to the accumulation position of FIG. 28, and to drain the burette, the handle is turned to the position of FIG. 27. To sample the fluid at the stopcock 74, the handle is turned to the position of FIG. 29.

Positioned adjacent the rear surface of the support panel 27, the ICP monitoring device is positioned on the support pole at the zero point on the reference scale. The device consists of a fluid-filled transducer manifold 95 with pressure sensitive tubing 96 leading from the transducer to the stopcock 15 and is connected into the ICP monitoring port 17. The pressure signals from the transducer are sent to a suitable monitoring device (not shown) by a cable 104 which is connected to the device 95 and has a suitable plug for connection for monitoring.

Figure 34:
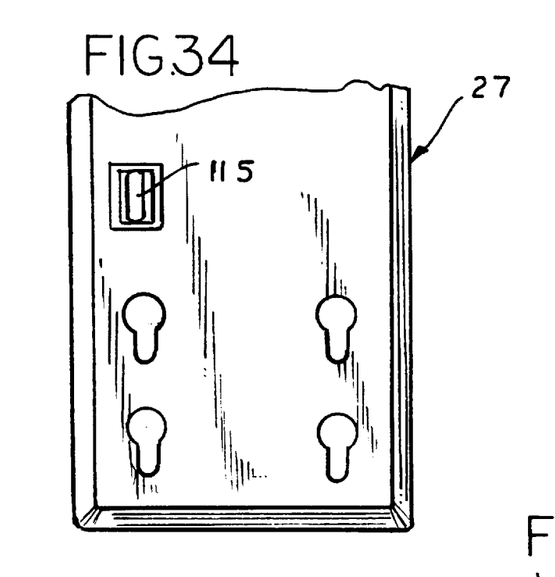
FIG. 34 is a front view of the lower end of the support panel showing the drainage bag mounting and strain relief member.
Figure 35:
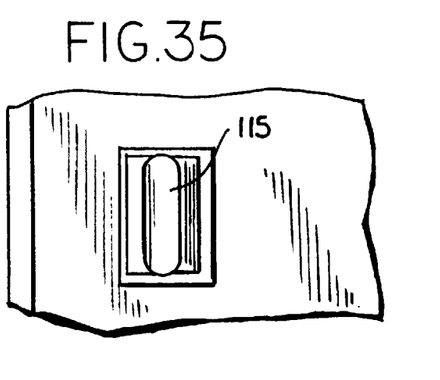
FIG. 35 is an enlarged front elevational view of the strain relief member of FIG. 34.
Figure 36:
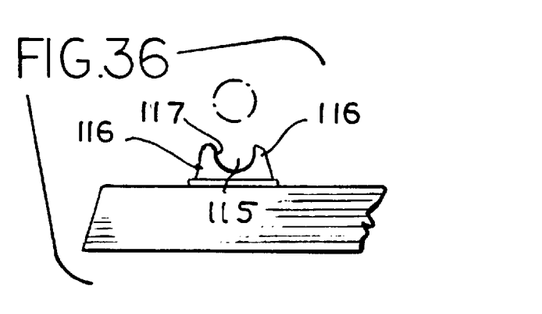
FIG. 36 is an enlarged end elevational view of the member of FIG. 34.
Figure 37:
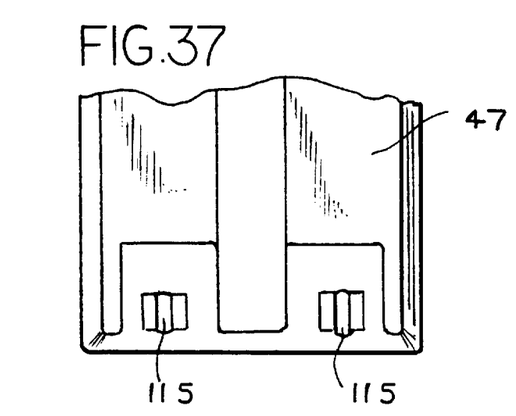
FIG. 37 is a view of the rear surface of the support panel showing the strain members on the back surface.

As shown in FIGS. 1, 2 and 3, there is a single stress relief member 90 positioned on the front of the panel 27 and a pair of stress relief members 91 formed on the rear surface 47 of the panel. These members, as well as member 53 on the sliding panel 43 are more clearly shown in FIGS. 34 through 39. The member 90 on the panel 27 as well as the member 53 are shown in FIGS. 34 through 36 and comprise an elongated groove 115 formed by raised sides 116 with slightly inturned edges 117 so that the tubing will snap into the groove 115. The pair of members 91, 91 shown in FIG. 37 are substantially identical in construction to that shown in FIGS. 34 through 36 with the elongated groove 115 having sides 116 with inturned edges 117 to allow a snap connection with tubing.

Thus, a new and novel drainage system has been shown and described having a number of features. Obviously, many forms of fluid-filled transducers along with alternative forms of ICP monitoring technology are available and may be utilized in the present device and, although a specific form of catheter and drainage shunt are shown in the drawings and described, other forms of the various devices in the system may be used and are contemplated in the claims.

We claim:

1. An external ventricular drainage system adapted for connection to a ventricular drainage catheter for placement in the ventricles of a patient's brain for receiving cerebrospinal fluid, said catheter being secured to the patient to prevent relative movement therebetween, said drainage system comprising tubing attached to the catheter and having valve means therein for controlling fluid flow therethrough, a needle-less sampling site positioned downstream of the valve means, a one-way valve following the sampling site, a length of flexible tubing connected to the one-way valve, and extending to a collection burette, a support panel mounted on an IV pole, a sliding panel having means for supporting said burette and mounted on said support panel, a high flow stopcock below the burette, and a drainage bag supported on said support panel and connected to said burette by said stopcock.

2. A drainage system as set forth in claim 1, in which said needle-less sampling site is formed in a Y-connection formed between the first-mentioned valve and said one-way valve, said sampling site being formed in one branch of the Y-connector and the flow connection to the one-way valve is provided in the other branch.

3. A drainage system as set forth in claim 1, in which said support panel is a substantially rigid member having a pressure scale thereon and a pair of openings formed in the upper end of the panel receiving a suspension cord extending through both openings and forming a loop for hanging on the IV pole.

4. A drainage system as set forth in claim 3, wherein a cord lock is provided on the cord to form the loop for suspension of the panel on the pole.

5. A drainage system as set forth in claim 1, wherein said support panel is provided with a pair of vertically spaced integral clamps formed to partially encompass the IV pole and a strap for each clamping member to secure the pole in the clamp.

6. A drainage system as set forth in claim 1, in which said sliding panel is formed with a front surface and a pair of arms extending from the sides of the surface to wrap around the support panel for frictional engagement therewith.

7. A drainage system as set forth in claim 6, wherein said panel arms are folded around the edges of said support panel and are suitably joined together on the rear surface of said support panel.

8. A drainage system as set forth in claim 6, in which a locking knob is threadingly engaged with the sliding panel and engages the front surface of said support panel to positively lock the sliding panel in operative position.

9. A drainage system as set forth in claim 6, in which said sliding panel is formed with an integral clamping means for said burette for support thereof and a sight window is formed in the sliding panel adjacent the burette.

10. A drainage system as set forth in claim 1, in which a pair of keyhole slots are formed adjacent the lower edge of said support panel, and said drainage bag is formed with a pair of integral buttons with reduced necks to be received in the keyhole slots.

11. A drainage system as set forth in claim 10, wherein a second pair of keyhole slots are positioned above the first pair of slots in said support panel for support of a second drainage bag during replacement of a full bag with an empty bag.

12. A drainage system as set forth in claim 1, wherein said burette is formed with an upper enlarged portion and a smaller diameter lower portion to allow more accurate measurement of the fluid entering the burette.

13. A drainage system as set forth in claim 1, wherein said high flow stopcock provides a needle-less sampling site below the burette.

14. A drainage system as set forth in claim 1 including tubing strain relief ribs formed on the rear surface of said support panel adjacent said drainage bag, a tubing relief rib formed on the rear surface of said sliding panel and a tubing strain relief rib formed in the front surface of said support panel.

15. A drainage system as set forth in claim 1, in which said support panel includes a pair of oppositely disposed leveling assist slots are formed in the opposite edges of said support panel, and a combination level and measuring tape has an extendable tape with a bent free end thereon for reception within one of the slots in the support panel.

16. A drainage system as set forth in claim 1, in which one of the ports of the first mentioned valve in the catheter is connected to a fluid pressure monitor.

17. A drainage system as set forth in claim 16, wherein said fluid pressure monitor is a fluid-filled strain gauge transducer connected to said first mentioned valve by tubing.

18. A drainage system as set forth in claim 2, in which said catheter is primed by the insertion of a syringe into the needle-less valve in said Y-connector.

* * * * *